United States Patent
Frazier et al.

(10) Patent No.: US 6,953,764 B2
(45) Date of Patent: Oct. 11, 2005

(54) HIGH ACTIVITY OLEFIN POLYMERIZATION CATALYST AND PROCESS

(75) Inventors: Kevin A. Frazier, Midland, MI (US); Harold Boone, Sugar Land, TX (US); Paul C. Vosejpka, Midland, MI (US); James C. Stevens, Richmond, TX (US)

(73) Assignee: Dow Global Technologies Inc., Midland, MI (US)

( * ) Notice: Subject to any disclaimer, the term of this patent is extended or adjusted under 35 U.S.C. 154(b) by 95 days.

(21) Appl. No.: 10/429,024

(22) Filed: May 2, 2003

(65) Prior Publication Data

US 2004/0220050 A1 Nov. 4, 2004

(51) Int. Cl.[7] .................. B01J 31/00; B01J 37/00; C08F 4/02; C08F 4/60
(52) U.S. Cl. .............. 502/103; 502/150; 502/152; 502/162; 502/167; 502/155; 546/2; 526/113
(58) Field of Search ................. 502/103, 155, 502/150, 152, 162, 167; 546/2; 526/113

(56) References Cited

U.S. PATENT DOCUMENTS

| | | | |
|---|---|---|---|
| 6,103,657 A | 8/2000 | Murray | |
| 6,258,903 B1 * | 7/2001 | Mawson et al. | 526/113 |
| 6,365,539 B1 * | 4/2002 | Ponasik et al. | 502/162 |
| 6,566,462 B2 * | 5/2003 | Murray et al. | 526/114 |
| 6,653,417 B2 * | 11/2003 | Peterson | 526/172 |
| 6,759,493 B1 * | 7/2004 | Nagy et al. | 526/161 |
| 6,767,975 B1 * | 7/2004 | Liu | 526/161 |
| 6,790,918 B2 * | 9/2004 | Nagy et al. | 526/161 |
| 2002/0142912 A1 | 10/2002 | Boussie et al. | |

FOREIGN PATENT DOCUMENTS

| | | | | |
|---|---|---|---|---|
| WO | WO 2000 020377 | 4/2000 | | |
| WO | WO 2002 038628 | 12/2002 | | |
| WO | WO 2004/024740 A1 * | 3/2004 | ............. | C07F/7/00 |

* cited by examiner

Primary Examiner—J. A. Lorengo
Assistant Examiner—Jennine Brown

(57) ABSTRACT

Group 4 metal complexes useful as addition polymerization catalysts of the formula:

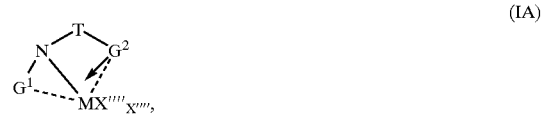

(IA)

wherein $G^1$ is a group containing from 1 to 40 atoms not counting hydrogen;

T is a divalent bridging group of from 10 to 30 atoms not counting hydrogen, selected from mono- or di-aryl-substituted methylene or silylene groups or mono- or di-heteroaryl-substituted methylene or silylene groups, wherein at least one such aryl- or heteroaryl-substituent is substituted in one or both ortho-positions with a secondary or tertiary alkyl-group, a secondary or tertiary heteroalkyl group, a cycloalkyl group, or a heterocycloalkyl group, $G^2$ is a $C_{6-20}$ heteroaryl group containing Lewis base functionality, M is the Group 4 metal, X"" is an anionic, neutral or dianionic ligand group, x"" is a number from 0 to 5, and bonds, optional bonds and electron donative interactions are represented by lines, dotted lines and arrows respectively.

10 Claims, No Drawings

HIGH ACTIVITY OLEFIN POLYMERIZATION CATALYST AND PROCESS

BACKGROUND OF THE INVENTION

This invention relates to a Group 4 metal complex, to a catalyst composition and to a process for polymerizing addition polymerizable unsaturated monomers, especially olefins. In particular, the invention is directed to certain Group 4 metal complexes, to catalyst compositions comprising the same, and to addition polymerization processes using the same.

Advances in polymerization and catalysis have resulted in the capability to produce many new polymers having improved physical and chemical properties useful in a wide variety of superior products and applications. With the development of new catalysts the choice of polymerization-type (solution, slurry, high pressure or gas phase) for producing a particular polymer has been greatly expanded. Also, advances in polymerization technology have provided more efficient, highly productive and economically enhanced processes. Recently, several new disclosures related to metal complexes based on donor ligands have published. Among these are U.S. Pat. No. 6,103,657, US2002 0142912, WO 2000 020377 and WO 2002 038628. Regardless of these technological advances in the polyolefin industry, common problems, as well as new challenges associated with process operability, still exist. For example, the tendency for known Group 4 metal complexes to lose catalyst operating efficiency at high polymerization temperatures in solution polymerization processes remains a challenge. Additionally, improved solubility of the metal complex in common aliphatic solvents is desired.

In particular, in a continuous solution polymerization process, operation at high polymerization temperatures, especially temperatures greater than 100° C., more preferably greater than 110° C., are desired in order to increase the operating efficiency of the process. In addition, by operating at elevated polymerization temperatures, olefin polymers having unique physical properties, composition, and structure may be prepared.

Thus, it would be advantageous to have a polymerization process capable of operating continuously with enhanced reactor efficiency and at the same time produce new and improved polymers. It would also be highly beneficial to have a continuously operating solution polymerization process having more stable catalyst productivity, improved efficiency, and increased duration of operation.

SUMMARY OF THE INVENTION

According to the present invention there is provided a Group 4 metal complex for use as a catalyst component of an addition polymerization catalyst composition, said metal complex corresponding to the formula:

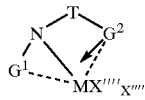

(IA)

wherein $G^1$ is selected from alkyl, cycloalkyl, aryl, aralkyl, alkaryl, heteroalkyl, heterocycloalkyl, heteroaryl, heteroaralkyl, heteroalkaryl, silyl, and inertly substituted derivatives thereof containing from 1 to 40 atoms not counting hydrogen, preferably a di-ortho-alkyl-substituted aryl, most preferably 2,6-diisopropylphenyl;

T is a divalent bridging group of from 10 to 30 atoms not counting hydrogen, selected from mono- or di-aryl-substituted methylene or silylene groups or mono- or di-heteroaryl-substituted methylene or silylene groups, wherein at least one such aryl- or heteroaryl-substituent is substituted in one or both ortho-positions with a secondary or tertiary alkyl-group, a secondary or tertiary heteroalkyl group, a cycloalkyl group, or a heterocycloalkyl group, $G^2$ is a $C_{6-20}$ heteroaryl group containing Lewis base functionality, especially a pyridin-2-yl- or substituted pyridin-2-yl group, M is the Group 4 metal, preferably hafnium, X"" is an anionic, neutral or dianionic ligand group, x"" is a number from 0 to 5 indicating the number of X"" groups, and bonds, optional bonds and electron donative interactions are represented by lines, dotted lines and arrows respectively.

Additionally, according to the present invention there is provided a catalyst composition comprising the foregoing Group 4 metal complex. Additional components of such catalyst composition may include an activator capable of converting said metal complex into an active catalyst for addition polymerization, a carrier or support, a liquid solvent or diluent, a tertiary component such as a scavenger, and/or one or more additives or adjuvants such as processing aids, sequestrants, and/or chain transfer agents.

In addition, the present invention provides an addition polymerizing process, especially an olefin polymerization process, wherein one or more addition polymerizable monomers are polymerized in the presence of the foregoing catalyst composition to form a high molecular weight polymer. Preferred polymerization processes are solution polymerizations, most preferably solution processes wherein ethylene, propylene, mixtures of ethylene and propylene, and mixtures of ethylene and/or propylene with one or more $C_4$ or higher olefins or diolefins are polymerized or copolymerized.

The metal complexes and catalysts of the invention may be used alone or combined with other metal complexes or catalyst compositions and the polymerization process may be used in a series or parallel process with one or more other polymerization processes. The invention also provides for a method of making a catalyst composition useful for the polymerization of olefin(s), comprising combining, contacting, blending and/or mixing the foregoing catalyst components, and, optionally, recovering the composition or removing diluent, if present, and recovering the resulting solid composition. Suitable additional polymerization catalyst compositions for use in combination with the metal complexes of the present invention include conventional Ziegler-Natta-type transition metal polymerization catalysts as well as π-bonded transition metal compounds such as metallocene-type catalysts, or other transition metal complexes. The catalysts of the invention are preferred for use as olefin polymerization catalysts compared to similar compounds lacking a secondary or tertiary branching center in T because they are capable of achieving higher catalyst efficiencies at a given monomer conversion or, alternatively, they are capable of achieving higher monomer conversion at a given catalyst efficiency.

DETAILED DESCRIPTION OF THE INVENTION

All reference to the Periodic Table of the Elements herein shall refer to the Periodic Table of the Elements, published and copyrighted by CRC Press, Inc., 2001. Also, any reference to a Group or Groups shall be to the Group or Groups as reflected in this Periodic Table of the Elements using the IUPAC system for numbering groups. For purposes of United States patent practice, the contents of any patent, patent application or publication referenced herein is hereby incorporated by reference in its entirety, especially with respect to the disclosure of analytical or synthetic techniques and general knowledge in the art.

The term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

The term "hetero" or "hetero-atom" refers to a non-carbon atom, especially Si, B, N, P or O. "Heteroaryl", "heteroalkyl", "heterocycloalkyl" and "heteroaralkyl" refer to aryl, alkyl, cycloalkyl, or aralkyl groups respectively, in which at least one carbon atom is replaced by a heteroatom. "Inertly substituted" refers to substituents on a ligand that do not destroy operability of the invention. Preferred inert substituents are halo, di($C_{1-6}$ hydrocarbyl)amino, $C_{2-6}$ hydrocarbyleneamino, $C_{1-6}$ halohydrocarbyl, and tri($C_{1-6}$ hydrocarbyl)silyl. The term "polymer", as used herein, includes both homopolymers, that is, polymers prepared from a single reactive compound, and copolymers, that is, polymers prepared by reaction of at least two polymer forming reactive, monomeric compounds. The term "crystalline" refers to a polymer that exhibits an X-ray diffraction pattern at 25° C. and possesses a first order transition or crystalline melting point (Tm) from the differential scanning calorimetry heating curve. The term may be used interchangeably with the term "semicrystalline".

The invention is directed toward novel metal complexes and catalyst compositions comprising the same. The invention also relates to a polymerization process having improved operability and product capabilities using the present metal complexes in the catalyst composition. It has been surprisingly discovered that using the present catalyst composition results in a substantially improved polymerization process. In particular, utilizing the present catalyst composition results in a substantial improvement in process operability, an ability to significantly increase the polymerization temperature, especially of a solution polymerization, improved catalyst performance, better polymer properties, and the capability to produce a broader range of polymers in a given reactor configuration.

Preferred metal complexes according to the present invention are those resulting from hydrogen elimination from the amine group, and optionally from the loss of one or more additional groups, especially from $G^2$, in polyfunctional Lewis base compounds of the following formula I:

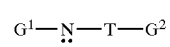
(I)

wherein $G^1$, T and $G^2$ are as previously defined for formula IA, upon reaction thereof with a Group 4 metal compound. Electron donation from the Lewis basic, heteroaryl functionality, $G^2$, preferably an electron pair, provides additional stability to the metal center of the metal complexes of formula IA.

Preferred examples of the foregoing polyfunctional Lewis base compounds and the resulting metal complexes correspond to the formulas:

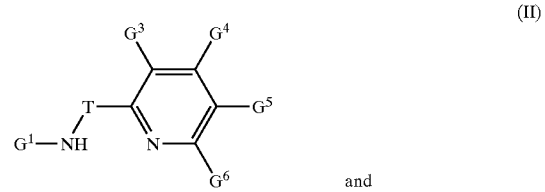
(II)

and

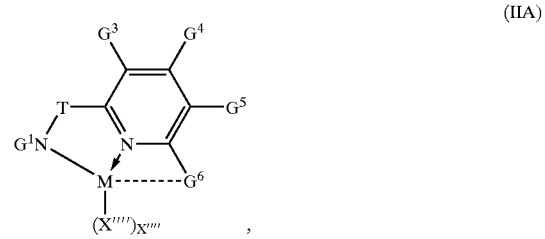
(IIA)

wherein
  M, X'''', x'''', $G^1$ and T are as previously defined,
  $G^3$, $G^4$, $G^5$ and $G^6$ are hydrogen, halo, or an alkyl, aryl, aralkyl, cycloalkyl, or silyl group, or a substituted alkyl-, aryl-, aralkyl-, cycloalkyl-, or silyl-group of up to 20 atoms not counting hydrogen, or adjacent $G^3$, $G^4$, $G^5$ or $G^6$ groups may be joined together thereby forming fused-ring derivatives, and
  bonds, optional bonds and electron pair donative interactions are represented by lines, dotted lines and arrows respectively.

More preferred examples of the foregoing difunctional Lewis base compounds and metal complexes correspond to the formula:

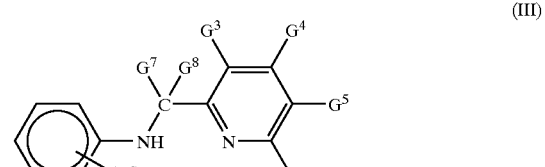
(III)

and

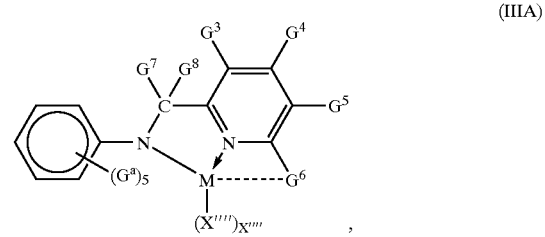
(IIIA)

wherein

M, X"", and x"" are as previously defined, $G^3$, $G^4$, and $G^5$ are as previously defined, preferably hydrogen or $C_{1-4}$ alkyl;

$G^6$ is $C_{6-20}$ aryl, aralkyl, alkaryl, or a divalent derivative thereof, most preferably naphthalenyl;

$G^a$ independently each occurrence is hydrogen, $C_{1-20}$ alkyl, or halo, more preferably at least 2 of said $G^a$ groups are $C_{1-20}$ alkyl groups bonded through a secondary or tertiary carbon atom and located in the two ortho-positions of the phenyl ring, most preferably both such $G^a$ groups are isopropyl groups located in the two ortho-positions of the phenyl ring;

$G^7$ and $G^8$ independently each occurrence are hydrogen or a $C_{1-30}$ alkyl, aryl, aralkyl, heteroalkyl, heteroaryl, or heteroaralkyl group, with the proviso that at least one of $G^7$ or $G^8$ is a $C_{10-30}$ aryl or heteroaryl group substituted in one or both ortho-positions with a secondary or tertiary alkyl- or cycloalkyl-ligand, most preferably one of $G^7$ and $G^8$ is hydrogen and the other is a phenyl, pyridinyl, naphthyl or anthracenyl group substituted at one or both of the ortho-positions (where possible) with an isopropyl, t-butyl, cyclopentyl, or cyclohexyl group, and bonds, optional bonds and electron pair donative interactions are represented by lines, dotted lines and arrows respectively.

Highly preferred polyfunctional Lewis base compounds and metal complexes for use herein correspond to the formula:

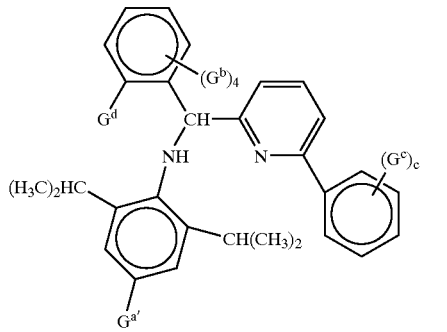

(IV)

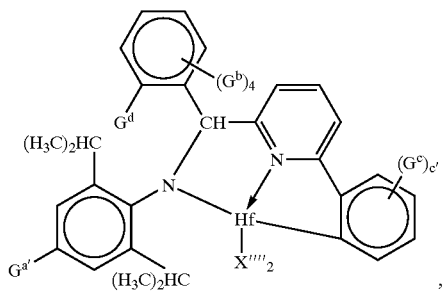

and (IVA)

wherein X"" each occurrence is halide, N,N-di($C_{1-4}$alkyl)amido, $C_{7-10}$ aralkyl, $C_{1-20}$ alkyl, $C_{5-20}$ cycloalkyl, or tri($C_{1-4}$)alkylsilyl; a tri($C_{1-4}$)alkylsilyl-substituted $C_{1-10}$ hydrocarbyl group; or two X"" groups together are a $C_{4-40}$ conjugated diene, and preferably each occurrence X"" is methyl, benzyl or tri(methyl)silylmethyl;

$G^{a'}$ is hydrogen, $C_{1-20}$ alkyl, or chloro;

$G^b$ independently each occurrence is hydrogen, $C_{1-20}$ alkyl, aryl, or aralkyl or two adjacent $R^b$ groups are joined together thereby forming a ring;

$G^c$ independently each occurrence is hydrogen, halo, $C_{1-20}$ alkyl, aryl, or aralkyl, or two adjacent $G^c$ groups are joined together thereby forming a ring, c is 1–5 and c' is 1–4; and $G^d$ is isopropyl or cyclohexyl.

Most highly preferred examples of metal complexes for use according to the present invention are complexes of the following formulas:

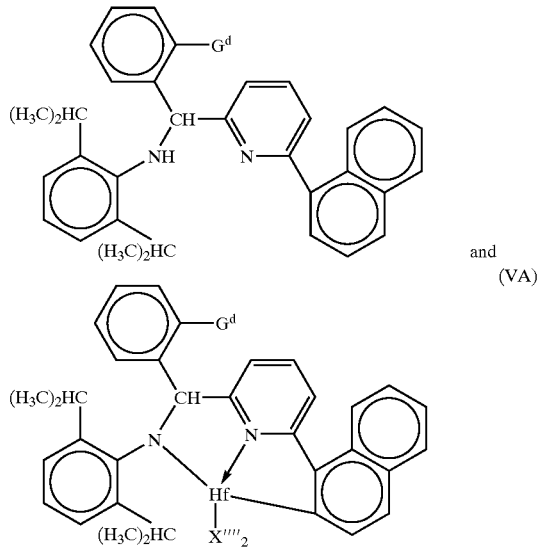

wherein X"" each occurrence is halide, N,N-dimethylamido, benzyl, $C_{1-20}$ alkyl, or tri(methyl)silyl-substituted alkyl, preferably each occurrence X"" is methyl, chloro, or tri(methyl)silylmethyl; and $G^d$ is isopropyl or cyclohexyl.

In another preferred embodiment of the invention, it has been discovered that the presence of one or more silyl-substituted hydrocarbyl X"" groups, such as tri(methyl)silylmethyl groups, improves the solubility of the metal complexes in aliphatic hydrocarbon diluents and results in extremely high polymerization efficiency.

It is expressly intended that the foregoing disclosure of preferred, more preferred, highly preferred, and most preferred embodiments of specific substituents with respect to any one of the foregoing formulas of the invention is applicable as well to any other of the preceding or succeeding formulas independent of any other substituent identity.

The above described metal complexes of the invention are typically activated in various ways to yield catalyst compounds having a vacant coordination site that will coordinate, insert, and polymerize addition polymerizable monomers, especially olefin(s). For the purposes of this patent specification and appended claims, the term "activator" is defined to be any compound or component or method which can activate any of the catalyst compounds of the invention as described above. Non-limiting examples of suitable activators include Lewis acids, non-coordinating ionic activators, ionizing activators, organometal compounds, and combinations of the foregoing substances that can convert a neutral catalyst compound to a catalytically active species.

It is believed, without desiring to be bound by such belief, that in one embodiment of the invention, catalyst activation may involve formation of a cationic, partially cationic, or zwitterionic species, by means of proton transfer, oxidation, or other suitable activation process. It is to be understood that the present invention is operable and fully enabled regardless of whether or not such an identifiable cationic, partially cationic, or zwitterionic species actually results during the activation process, also interchangeably referred to herein as an "ionization" process or "ionic activator".

One suitable class of organometal activators or cocatalysts are alumoxanes, also referred to as alkylaluminoxanes. Alumoxanes are well known activators for use with metallocene type catalyst compounds to prepare addition polymerization catalysts. There are a variety of methods for preparing alumoxanes and modified alumoxanes, non-limiting examples of which are described in U.S. Pat. Nos. 4,665,208, 4,952,540, 5,091,352, 5,206,199, 5,204,419, 4,874,734, 4,924, 018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451 5,744,656; European publications EP-A-561476, EP-A-279586 and EP-A-594218; and PCT publication WO 94/10180. Preferred alumoxanes are tri($C_{3-6}$)alkylalmunium modified methylalumoxane, especially tri(isobutyl) aluminum modified methylalumoxane, available commercially as MMAO-3A, from Akzo Nobel, Inc.

It is within the scope of this invention to use alumoxane(s) or modified alumoxane(s) as an activator or as a tertiary component in the invented process. That is, the compound may be used alone or in combination with other activators, neutral or ionic, such as tri(alkyl)ammonium tetrakis (pentafluorophenyl)borate compounds, trisperfluoroaryl compounds, polyhalogenated heteroborane anions (WO 98/43983), and combinations thereof. When used as a tertiary component, the amount of alumoxane employed is generally less than that necessary to effectively activate the metal complex when employed alone. In this embodiment, it is believed, without wishing to be bound by such belief, that the alumoxane does not contribute significantly to actual catalyst activation. Not withstanding the foregoing, it is to be understood that some participation of the alumoxane in the activation process is not necessarily excluded.

Ionizing cocatalysts may contain an active proton, or some other cation associated with, but not coordinated to or only loosely coordinated to, an anion of the ionizing compound. Such compounds and the like are described in European publications EP-A-570982, EP-A-520732, EP-A-495375, EP-A-500944, EP-A-277 003 and EP-A-277004, and U.S. Pat. Nos. 5,153,157, 5,198,401, 5,066,741, 5,206, 197, 5,241,025, 5,384,299 and 5,502,124. Preferred among the foregoing activators are ammonium cation containing salts, especially those containing trihydrocarbyl-substituted ammonium cations containing one or two $C_{10-40}$ alkyl groups, especially methylbis(octadecyl)ammonium- and methylbis(tetradecyl)ammonium-cations and a non-coordinating anion, especially a tetrakis(perfluoro) arylborate anion, especially tetrakis(pentafluorophenyl) borate. It is further understood that the cation may comprise a mixture of hydrocarbyl groups of differing lengths. For example, the protonated ammonium cation derived from the commercially available long-chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT. A most preferred ammonium salt activator is methyldi($C_{14-20}$alkyl) ammonium tetrakis(pentafluorophenyl)borate.

Activation methods using ionizing ionic compounds not containing an active proton but capable of forming active catalyst compositions, such as ferrocenium salts of the foregoing non-coordinating anions are also contemplated for use herein, and are described in EP-A-426637, EP-A-573403 and U.S. Pat. No. 5,387,568.

A class of cocatalysts comprising non-coordinating anions generically referred to as expanded anions, further disclosed in U.S. Pat. No. 6,395,671, may be suitably employed to activate the metal complexes of the present invention for olefin polymerization. Generally, these cocatalysts (illustrated by those having imidazolide, substituted imidazolide, imidazolinide, substituted imidazolinide, benzimidazolide, or substituted benzimidazolide anions) may be depicted as follows:

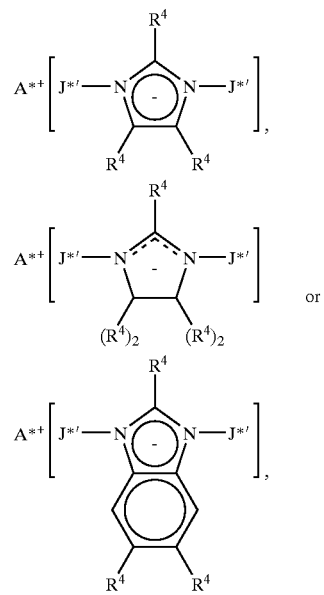

wherein:
$A^{*+}$ is a cation, especially a proton containing cation, and preferably is a trihydrocarbyl ammonium cation containing one or two $C_{10-40}$ alkyl groups, especially a methyldi($C_{14-20}$alkyl)ammonium-cation, $R^4$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^{*\prime}$ is tris(pentafluorophenyl)borane or tris (pentafluorophenyl)alumane).

Examples of these catalyst activators include trihydrocarbylammonium-salts, especially, methyldi($C_{14-20}$alkyl)ammonium-salts of: bis(tris(pentafluorophenyl) borane)imidazolide, bis(tris(pentafluorophenyl)borane)-2-undecylimidazolide, bis(tris(pentafluorophenyl)borane)-2-heptadecylimidazolide, bis(tris(pentafluorophenyl)borane)-4,5-bis(undecyl)imidazolide, bis(tris(pentafluorophenyl) borane)-4,5-bis(heptadecyl)imidazolide, bis(tris (pentafluorophenyl)borane)imidazolinide, bis(tris (pentafluorophenyl)borane)-2-undecylimidazolinide, bis (tris(pentafluorophenyl)borane)-2-heptadecylimidazolinide, bis(tris(pentafluorophenyl)borane)-4,5-bis(undecyl) imidazolinide, bis(tris(pentafluorophenyl)borane)-4,5-bis (heptadecyl)imidazolinide, bis(tris(pentafluorophenyl) borane)-5,6-dimethylbenzimidazolide, bis(tris (pentafluorophenyl)borane)-5,6-bis(undecyl) benzimidazolide, bis(tris(pentafluorophenyl)alumane) imidazolide; bis(tris(pentafluorophenyl)alumane)-2- undecylimidazolide, bis(tris(pentafluorophenyl)alumane)-2-heptadecylimidazolide, bis(tris(pentafluorophenyl)alumane)-4,5-bis(undecyl)imidazolide, bis(tris(pentafluorophenyl)alumane)-4,5-bis(heptadecyl)imidazolide, bis(tris(pentafluorophenyl)alumane)-2-imidazolinide, bis(tris(pentafluorophenyl)alumane)-2-undecylimidazolinide, bis(tris(pentafluorophenyl)alumane)-2-heptadecylimidazolinide, bis(tris(pentafluorophenyl)alumane)-4,5-bis(undecyl)imidazolinide, bis(tris(pentafluorophenyl)alumane)-4,5-bis(heptadecyl)imidazolinide, bis(tris(pentafluorophenyl)alumane)-5,6-dimethylbenzimidazolide, and bis(tris(pentafluorophenyl)alumane)-5,6-bis(undecyl)benzimidazolide.

Other activators include those described in PCT publication WO 98/07515 such as tris (2,2',2"-nonafluorobiphenyl) fluoroaluminate. Combinations of activators are also contemplated by the invention, for example, alumoxanes and ionizing activators in combinations, see for example, EP-A-0 573120, PCT publications WO 94/07928 and WO 95/14044 and U.S. Pat. Nos. 5,153,157 and 5,453,410. WO 98/09996 describes activating catalyst compounds with perchlorates, periodates and iodates, including their hydrates. WO 99/18135 describes the use of organoboroaluminum activators. EP-A-781299 describes using a sylilum salt in combination with a non-coordinating compatible anion. Other activators or methods for activating a catalyst compound are described in for example, U.S. Pat. Nos. 5,849,852, 5,859,653, 5,869,723, EP-A-615981, and PCT publication WO 98/32775.

It is also within the scope of this invention that the above described metal complexes can be combined with more than one of the activators or activation methods described above. The mole ratio of the activator component(s) to the metal complex in the catalyst compositions of the invention suitably is in the range of between 0.3:1 to 2000:1, preferably 1:1 to 800:1, and most preferably 1:1 to 500:1. Where the activator is an ionizing activator such as those based on the anion tetrakis(pentafluorophenyl)boron or the strong Lewis acid trispentafluorophenylboron, the mole ratio of the metal or metalloid of the activator component to the metal complex is preferably in the range of between 0.3:1 to 3:1.

Tertiary Components

In addition to the metal complex and cocatalyst or activator, it is contemplated that certain tertiary components or mixtures thereof may be added to the catalyst composition or the reaction mixture in order to obtain improved catalyst performance or other benefit. Examples of such tertiary components include scavengers designed to react with contaminants in the reaction mixture to prevent catalyst deactivation. Suitable tertiary components may also activate or assist in activation of one or more of the metal complexes employed in the catalyst composition.

Examples include Lewis acids, such as trialkylaluminum compounds, dialkylzinc compounds, dialkylaluminumalkoxides, dialkylaluminumaryloxides, dialkylaluminum N,N-dialkylamides, di(trialkylsilyl)aluminum N,N-dialkylamides, dialkylaluminum N,N-di(trialkylsilyl)amides, alkylaluminumdialkoxides, alkylaluminum di(N,N-dialkylamides), tri(alkyl)silylaluminum N,N-dialkylamides, alkylaluminum N,N-di(trialkylsilyl) amides, alkylaluminum diaryloxides, alkylaluminum $\mu$-bridged bis(amides) such as bis(ethylaluminum)-1-phenylene-2-(phenyl)amido $\mu$-bis(diphenylamide), and/or alumoxanes; as well as Lewis bases, such as organic ether, polyether, amine, and polyamine compounds. Many of the foregoing compounds and their use in polymerizations is disclosed in U.S. Pat. Nos. 5,712,352 and 5,763,543, and in WO 96/08520. Preferred examples of the foregoing tertiary components include trialkylaluminum compounds, dialkylaluminum aryloxides, alkylaluminum diaryloxides, dialkylaluminum amides, alkylaluminum diamides, dialkylaluminum tri(hydrocarbylsilyl)amides, alkylaluminum bis(tri(hydrocarbylsilyl)amides), alumoxanes, and modified alumoxanes. Highly preferred tertiary components are alumoxanes, modified alumoxanes, or compounds corresponding to the formula $R^e{}_2Al(OR^f)$ or $R^e{}_2Al(NR^g{}_2)$ wherein $R^e$ is $C_{1-20}$ alkyl, $R^f$ independently each occurrence is $C_{6-20}$ aryl, preferably phenyl or 2,6-di-t-butyl-4-methylphenyl, and $R^g$ is $C_{1-4}$ alkyl or tri($C_{1-4}$alkyl)silyl, preferably trimethylsilyl. Most highly preferred tertiary components include methylalumoxane, tri(isobutylaluminum)-modified methylalumoxane, di(n-octyl)aluminum 2,6-di-t-butyl-4-methylphenoxide, and di(2-methylpropyl)aluminum N,N-bis(trimethylsilyl)amide.

Another example of a suitable tertiary component is a hydroxycarboxylate metal salt, by which is meant any hydroxy-substituted, mono-, di- or tri-carboxylic acid salt wherein the metal portion is a cationic derivative of a metal from Groups 1–13 of the Periodic Table of Elements. This compound may be used to improve polymer morphology especially in a gas phase polymerization. Non-limiting examples include saturated, unsaturated, aliphatic, aromatic or saturated cyclic, substituted carboxylic acid salts where the carboxylate ligand has from one to three hydroxy substituents and from 1 to 24 carbon atoms. Examples include hydroxyacetate, hydroxypropionate, hydroxybutyrate, hydroxyvalerate, hydroxypivalate, hydroxycaproate, hydroxycaprylate, hydroxyheptanate, hydroxypelargonate, hydroxyundecanoate, hydroxyoleate, hydroxyoctoate, hydroxyalmitate, hydroxymyristate, hydroxymargarate, hydroxystearate, hydroxyarachate and hydroxytercosanoate. Non-limiting examples of the metal portion includes a metal selected from the group consisting of Al, Mg, Ca, Sr, Sn, Ti, V, Ba, Zn, Cd, Hg, Mn, Fe, Co, Ni, Pd, Li and Na. Preferred metal salts are zinc salts.

In one embodiment, the hydroxycarboxylate metal salt is represented by the following general formula:

$M(Q)_x(OOCR)_y$, where

M is a metal from Groups 1 to 16 and the Lanthanide and Actinide series, preferably from Groups 1 to 7 and 12 to 16, more preferably from Groups 3 to 7 and 12 to 14, even more preferably Group 12, and most preferably Zn;

Q is halogen, hydrogen, hydroxide, or an alkyl, alkoxy, aryloxy, siloxy, silane, sulfonate or siloxane group of up to 20 atoms not counting hydrogen;

R is a hydrocarbyl radical having from 1 to 50 carbon atoms, preferably 1 to 20 carbon atoms, and optionally substituted with one or more hydroxy, alkoxy, N,N-dihydrocarbylamino, or halo groups, with the proviso that in one occurrence R is substituted with a hydroxy- or N,N-dihydrocarbylamino-group, preferably a hydroxy-group that is coordinated to the metal, M by means of unshared electrons thereof;

x is an integer from 0 to 3;

y is an integer from 1 to 4.

In a preferred embodiment M is Zn, x is 0 and y is 2.

Preferred examples of the foregoing hydroxycarboxylate metal salts include compounds of the formulas:

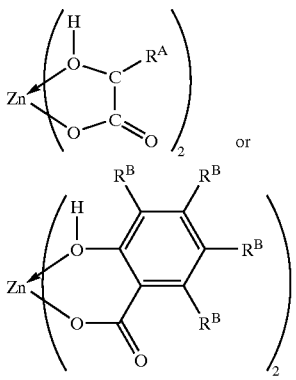

wherein $R^A$ and $R^B$ independently each occurrence are hydrogen, halogen, or $C_{1-6}$ alkyl.

Other additives may be incorporated into the catalyst compositions or employed simultaneously in the polymerization reaction for one or more beneficial purposes. Examples of additives that are known in the art include metal salts of fatty acids, such as aluminum, zinc, calcium, titanium or magnesium mono, di- and tri-stearates, octoates, oleates and cyclohexylbutyrates. Examples of such additives include Witco Aluminum Stearate #18, Witco Aluminum Stearate #22, Witco Aluminum Stearate #132 and Witco Aluminum Stearate EA Food Grade, all of which are available from Witco Corporation, Memphis, Tenn., USA. The use of such additives in a catalyst composition is disclosed in U.S. Pat. No. 6,306,984.

Additional suitable additives include antistatic agents such as fatty amines, for example, Kemamine AS 990/2 zinc additive, a blend of ethoxylated stearyl amine and zinc stearate, or Kemamine AS 990/3, a blend of ethoxylated stearyl amine, zinc stearate, and octadecyl-3,5-di-tert-butyl-4-hydroxyhydrocinnamate, also available from Witco Corporation, Memphis, Tenn., USA.

The above described catalyst compounds and catalyst compositions may be combined with one or more support materials or carriers using one of the support methods well known in the art or as described below. Such supported catalysts are particularly useful for slurry or gas phase polymerizations. Either the catalyst composition or the individual components thereof may be in a supported form, for example deposited on, contacted with, or incorporated within a support or carrier.

The terms "support" or "carrier" are used interchangeably and are any porous or non-porous support material, preferably a porous support material, for example, inorganic oxides, carbides, nitrides, and halides. Other carriers include resinous support materials such as polystyrene, a functionalized or crosslinked organic supports, such as polystyrene divinyl benzene polyolefins or polymeric compounds, or any other organic or inorganic support material and the like, or mixtures thereof.

The preferred carriers are inorganic oxides that include those Group 2, 3, 4, 5, 13 or 14 metal oxides. The preferred supports includes silica, alumina, silica-alumina, silicon carbide, boron nitride, and mixtures thereof. Other useful supports include magnesia, titania, zirconia, and clays. Also, combinations of these support materials may be used, for example, silica-chromium and silica-titania.

It is preferred that the carrier has a surface area in the range of from about 10 to about 700 $m^2/g$, pore volume in the range of from about 0.1 to about 4.0 cc/g and average particle size in the range of from about 10 to about 500 $\mu m$.

More preferably, the surface area of the carrier is in the range of from about 50 to about 500 $m^2/g$, pore volume of from about 0.5 to about 3.5 cc/g, and average particle size of from about 20 to about 200 $\mu m$. Most preferably the surface area of the carrier is in the range of from about 100 to about 400 $m^2/g$, pore volume from about 0.8 to about 3.0 cc/g and average particle size is from about 20 to about 100 $\mu m$. The average pore size of a carrier of the invention is typically in the range of from about 1 to 100 nm, preferably 5 to 50 nm, and most preferably 7.5 to 35 nm.

Examples of supported catalyst compositions suitably employed in the present invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664; and PCT publications WO 95/32995, WO 95/14044, WO 96/06187 and WO 97/02297.

Examples of supporting conventional-type catalyst compositions that may also be employed in the present invention are described in U.S. Pat. Nos. 4,894,424, 4,376,062, 4,395,359, 4,379,759, 4,405,495 4,540758 and 5,096,869.

It is contemplated that the catalyst compounds of the invention may be deposited on the same or separate supports together with an activator, or the activator may be used in an unsupported form, or may be deposited on a support different from the supported catalyst compounds of the invention, or any combination thereof.

There are various other methods in the art for supporting a polymerization catalyst compound or catalyst compositions suitable for use in the present invention. For example, the catalyst compound of the invention may contain a polymer bound ligand as described in U.S. Pat. Nos. 5,473,202 and 5,770,755. The catalyst composition of the present invention may be spray dried as described in U.S. Pat. No. 5,648,310. The support used with the catalyst composition of the invention may be functionalized as described in European publication EP-A-802 203. Finally, at least one substituent or leaving group of the catalyst may be selected as described in U.S. Pat. No. 5,688,880.

In a preferred embodiment, the invention provides for a supported catalyst composition that includes a surface modifier as described in PCT publication WO 96/11960.

A preferred method for producing a supported catalyst composition according to the invention is described in PCT publications WO 96/00245 and WO 96/00243. In this preferred method, the catalyst compound and activators are combined in separate liquid. The liquids may be any compatible solvent or other liquid capable of forming a solution or slurry with the catalyst compounds and/or activator. In the most preferred embodiment the liquids are the same linear or cyclic aliphatic or aromatic hydrocarbon, most preferably toluene. The catalyst compound and activator mixtures or solutions are mixed together and added to a porous support or, alternatively, the porous support is added to the respective mixtures. The resulting supported composition may be dried to remove diluent, if desired, or utilized separately or in combination in a polymerization. Highly desirably the total volume of the catalyst compound solution and the activator solution or the mixtures thereof is less than five times the pore volume of the porous support, more preferably less than four times, even more preferably less than three times; with most prefer ranges being from 1.1 times to 3.5 times the pore volume of the support.

Procedures for measuring the total pore volume of a porous support are well known in the art. The preferred procedure is BET nitrogen absorption. Another suitable method well known in the art is described in Innes, Total Porosity and Particle Density of Fluid Catalysts By Liquid Titration, *Analytical Chemistry*, (1956) 28, 332–334.

It is further contemplated by the invention that other catalysts can be combined with the catalyst compounds of the invention. Examples of such other catalysts are disclosed in U.S. Pat. Nos. 4,937,299, 4,935,474, 5,281,679, 5,359,015, 5,470,811, 5,719,241, 4,159,965, 4,325,837, 4,701,432, 5,124,418, 5,077,255, 5,183,867, 5,391,660, 5,395,810, 5,691,264, 5,723, 399 and 5,767,031; and PCT Publication WO 96/23010. In particular, the compounds that may be combined with the metal complexes of the invention to produce mixtures of polymers in one embodiment of the invention include conventional Ziegler-Natta transition metal compounds and coordination complexes.

Conventional Ziegler-Natta transition metal compounds include the well known magnesium dichloride supported compounds, vanadium compounds, and chromium catalysts (also known as "Phillips type catalysts"). Examples of these conventional-type transition metal catalysts are discussed in U.S. Pat. Nos. 4,115,639, 4,077,904 4,482,687, 4,564,605, 4,721,763, 4,879,359 and 4,960,741. The conventional-type transition metal catalyst compounds that may be used in the present invention include transition metal compounds from Groups 3 to 8, preferably Group 4 of the Periodic Table of Elements.

Suitable Ziegler-Natta catalyst compounds include alkoxy, phenoxy, bromide, chloride and fluoride derivatives of the foregoing metals, especially titanium. Preferred titanium compounds include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3 \cdot \frac{1}{3}AlCl_3$ and $Ti(OC_{12}H_{25})Cl_3$, and mixtures thereof, preferably supported on an inert support, usually $MgCl_2$. Other examples are described in, U.S. Pat. Nos. 4,302,565, 4,302,566, and 6,124,507, for example.

Non-limiting examples of vanadium catalyst compounds include vanadyl trihalide, alkoxy halides and alkoxides such as $VOCl_3$, $VOCl_2(OBu)$ where Bu is butyl and $VO(OC_2H_5)_3$; vanadium tetra-halide and vanadium alkoxy halides such as $VCl_4$ and $VCl_3(OBu)$; vanadium and vanadyl acetyl acetonates and chloroacetyl acetonates such as $V(AcAc)_3$ and $VOCl_2(AcAc)$ where (AcAc) is an acetyl acetonate.

Conventional-type chromium catalyst compounds suitable for use in the present invention include $CrO_3$, chromocene, silyl chromate, chromyl chloride ($CrO_2Cl_2$), chromium-2-ethyl-hexanoate, chromium acetylacetonate ($Cr(AcAc)_3$), and the like. Non-limiting examples are disclosed in U.S. Pat. Nos. 2,285,721, 3,242,099 and 3,231,550.

Still other conventional-type transition metal catalyst compounds suitable for use in the present invention are disclosed in U.S. Pat. Nos. 4,124,532, 4,302,565, 4,302,566 and 5,763,723 and EP-A-416815 and EP-A-420436.

Cocatalyst compounds for use with the above conventional-type catalyst compounds are typically organo-metallic derivatives of metals of Groups 1, 2, 12 or 13. Non-limiting examples include methyllithium, butyllithium, dihexylmercury, butylmagnesium, diethylcadmium, benzylpotassium, diethylzinc, tri-n-butylaluminum, diisobutyl ethylboron, diethylcadmium, di-n-butylzinc and tri-n-amylboron, and, in particular, aluminum trialkyl compounds, such as tri-hexylaluminum, triethylaluminum, trimethylaluminum, and triisobutylaluminum. Other suitable cocatalyst compounds include mono-organohalides and hydrides of Group 13 metals, and mono- or di-organohalides and hydrides of Group 13 metals. Non-limiting examples of such conventional-type cocatalyst compounds include di-isobutylaluminum bromide, isobutylboron dichloride, methyl magnesium chloride, ethylberyllium chloride, ethylcalcium bromide, di-isobutylaluminum hydride, methylcadmium hydride, diethylboron hydride, hexylberyllium hydride, dipropylboron hydride, octylmagnesium hydride, butylzinc hydride, dichloroboron hydride, dibromoaluminum hydride and bromocadmium hydride. Conventional-type organometallic cocatalyst compounds are known to those in the art and a more complete discussion of these compounds may be found in U.S. Pat. Nos. 3,221,002 and 5,093,415.

Coordination complexes include metallocene catalyst compounds, which are half and full sandwich compounds having one or more π-bonded ligands including cyclopentadienyl-type structures or other similar functioning structure such as pentadiene, cyclooctatetraendiyl and imides. Typical compounds are generally described as coordination complexes containing one or more ligands capable of π-bonding to a transition metal atom, usually, cyclopentadienyl derived ligands or moieties, in combination with a transition metal selected from Group 3 to 8, preferably 4, 5 or 6 or from the lanthanide and actinide series of the Periodic Table of Elements. Exemplary of metallocene-type catalyst compounds are described in, for example, U.S. Pat. Nos. 4,530,914, 4,871,705, 4,937,299, 5,017,714, 5,055,438, 5,096,867, 5,120,867, 5,124,418, 5,198,401, 5,210,352, 5,229,478, 5,264,405, 5,278,264, 5,278,119, 5,304,614, 5,324,800, 5,347,025, 5,350,723, 5,384,299, 5,391,790, 5,391,789, 5,399,636, 5,408,017, 5,491,207, 5,455,366, 5,534,473, 5,539,124, 5,554,775, 5,621,126, 5,684,098, 5,693,730, 5,698,634, 5,710,297, 5,712,354, 5,714,427, 5,714,555, 5,728,641, 5,728,839, 5,753,577, 5,767,209, 5,770,753 and 5,770,664; European publications: EP-A-0 591 756, EP-A-0 520 732, EP-A-0 420 436, EP-A-0 485 822, EP-A-0 485 823, EP-A-0 743 324, EP-A-0 518 092; and PCT publications: WO 91/04257, WO 92/00333, WO 93/08221, WO 93/08199, WO 94/01471, WO 96/20233, WO 97/15582, WO 97/19959, WO 97/46567, WO 98/01455, WO 98/06759 and WO 98/011144.

Preferred examples of meteallocenes used in combination with the metal complexes of the present invention include compounds of the formulas:

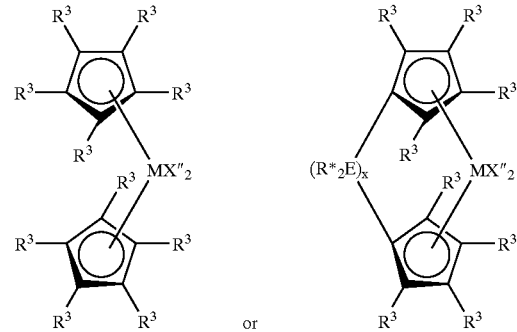

wherein:
M is titanium, zirconium or hafnium, preferably zirconium or hafnium, in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (i.e., a hydrocarbadiyl, siladiyl or germadiyl group) thereby forming a fused-ring system, X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state, R* independently each occurrence is $C_{1-4}$ alkyl or phenyl, E independently each occurrence is carbon or silicon, and x is an integer from 1 to 8.

Additional examples of coordination complexes used in combination with the metal complexes of the present invention are those of the formula:

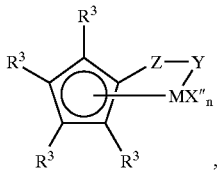

wherein:

M is titanium, zirconium or hafnium in the +2, +3 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (i.e., a hydrocarbadiyl, siladiyl or germadiyl group) thereby forming a fused-ring system, each X" is a halo, hydrocarbyl, hydrocarbyloxy, hydrocarbylamino, or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein R* is as previously defined, and n is an integer from 1 to 3.

The foregoing types of coordination complexes are described in, for example, U.S. Pat. Nos. 5,703,187, 5,965,756, 6,150,297, 5,064,802, 5,145,819, 5,149,819, 5,243,001, 5,239,022, 5,276,208, 5,296,434, 5,321,106, 5,329,031, 5,304,614, 5,677,401 and 5,723,398, PCT publications WO 93/08221, WO 93/08199, WO 95/07140, WO 98/11144, WO02/02577, WO 02/38628; and European publications EP-A-578838, EP-A-638595, EP-A-513380 and EP-A-816372.

Additional suitable metal coordination complexes used in combination with the metal complexes of the present invention are complexes of a transition metal, a substituted or unsubstituted π-bonded ligand, and one or more heteroallyl moieties, such as those described in U.S. Pat. Nos. 5,527,752 and 5,747,406, and EP-B-0 735 057. Preferably, these catalyst compounds are represented by one of the following formulas:

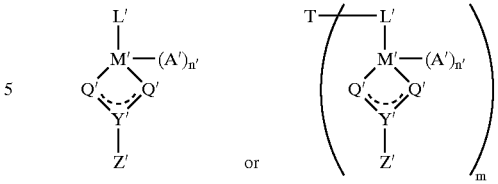

wherein M' is a metal from Groups 4, 5 or 6 or the Periodic Table of the Elements, preferably titanium, zirconium or hafnium, most preferably zirconium or hafnium;

L' is a substituted or unsubstituted, π-bonded ligand coordinated to M' and, when T is present, bonded to T, preferably L' is a cycloalkadienyl ligand, optionally with one or more hydrocarbyl substituent groups having from 1 to 20 carbon atoms, or fused-ring derivatives thereof, for example, a cyclopentadienyl, indenyl or fluorenyl ligand;

each Q' is independently selected from the group consisting of —O—, —NR'—, —CR'$_2$— and —S—, preferably oxygen;

Y' is either C or S, preferably carbon;

Z' is selected from the group consisting of —OR', —NR'$_2$, —CR'$_3$, —SR', —SiR'$_3$, —PR'$_2$, —H, and substituted or unsubstituted aryl groups, with the proviso that when Q is —NR'— then Z is selected from the group consisting of: —OR', —NR'$_2$, —SR', —SiR'$_3$, —PR'$_2$ and —H, preferably Z is selected from the group consisting of —OR', —CR'$_3$ and —NR'$_2$;

n' is 1 or 2, preferably 1;

A' is a univalent anionic group when n is 2 or A' is a divalent anionic group when n is 1, preferably A' is a carbamate, hydroxycarboxylate, or other heteroallyl moiety described by the Q', Y' and Z' combination;

each R' is independently a group containing carbon, silicon, nitrogen, oxygen, and/or phosphorus and one or more R' groups may be also attached to the L' substituent, preferably R' is a hydrocarbon group containing from 1 to 20 carbon atoms, most preferably an alkyl, cycloalkyl, or an aryl group;

T is a bridging group selected from the group consisting of alkylene and arylene groups containing from 1 to 10 carbon atoms optionally substituted with carbon or heteroatom(s), germanium, silicon and alkyl phosphine; and m is 2 to 7, preferably 2 to 6, most preferably 2 or 3.

In the foregoing formulas, the supportive substituent formed by Q', Y' and Z' is a uncharged polydentate ligand exerting electronic effects due to its high polarizability, similar to the cyclopentadienyl ligand. In the most referred embodiments of this invention, the disubstituted carbamates and the hydroxycarboxylates are employed. Non-limiting examples of these catalyst compounds include indenyl zirconium tris(diethylcarbamate), indenyl zirconium tris (trimethylacetate), indenyl zirconium tris(p-toluate), indenyl zirconium tris(benzoate), (1-methylindenyl)zirconium tris (trimethylacetate), (2-methylindenyl) zirconium tris (diethylcarbamate), (methylcyclopentadienyl)zirconium tris (trimethylacetate), cyclopentadienyl tris(trimethylacetate), tetrahydroindenyl zirconium tris(trimethylacetate), and (pentamethyl-cyclopentadienyl)zirconium tris(benzoate). Preferred examples are indenyl zirconium tris (diethylcarbamate), indenylzirconium tris(trimethylacetate), and (methylcyclopentadienyl)zirconium tris (trimethylacetate).

In another embodiment of the invention the additional catalyst compounds are those nitrogen containing heterocyclic ligand complexes, based on bidentate ligands containing pyridine or quinoline moieties, such as those described in WO 96/33202, WO 99/01481, WO 98/42664 and U.S. Pat. No. 5,637,660.

It is within the scope of this invention, in one embodiment, that catalyst compound complexes of $Ni^{2+}$ and $Pd^{2+}$ described in the articles Johnson, et al., "New Pd(II)- and Ni(II)-Based Catalysts for Polymerization of Ethylene and a-Olefins", *J.A.C.S.* (1995) 117, 6414–6415 and Johnson, et al., "Copolymerization of Ethylene and Propylene with Functionalized Vinyl Monomers by Palladium(II) Catalysts", *J.A.C.S.*, (1996) 118, 267–268, and WO 96/23010, may be combined with the present metal complexes for use in the process of the invention. These complexes can be either dialkyl ether adducts, or alkylated reaction products of the described dihalide complexes that can be activated to a cationic state by the conventional-type cocatalysts or the activators of this invention described below.

Additional suitable catalyst compounds for use in the foregoing mixed catalyst compositions are diimine based ligands containing Group 8 to 10 metal compounds disclosed in PCT publications WO 96/23010 and WO 97/48735 and Gibson, et al., *Chem. Comm.*, (1998) 849–850.

Other catalysts are those Group 5 and 6 metal imido complexes described in EP-A-0 816 384 and U.S. Pat. No. 5,851,945. In addition, catalysts include bridged bis (arylamido) Group 4 compounds described by D. H. McConville, et al., *Organometallics* (1995) 14, 5478–5480. Other catalysts are described as bis(hydroxy aromatic nitrogen ligands) in U.S. Pat. No. 5,852,146. Other metallocene-type catalysts containing one or more Group 15 atoms include those described in WO 98/46651. Still another metallocene-type catalysts include those multinuclear catalysts as described in WO 99/20665.

It is contemplated in some embodiments, that the catalyst compounds employed in addition to those of the invention described above may be asymmetrically substituted in terms of additional substituents or types of substituents, and/or unbalanced in terms of the number of additional substituents on the π-bonded ligand groups. It is also contemplated that such additional catalysts may include their structural or optical or enantiomeric isomers (meso and racemic isomers) and mixtures thereof, or they may be chiral and/or a bridged catalyst compounds.

In one embodiment of the invention, one or more olefins, preferably one or more $C_{2-30}$ olefins, preferably ethylene and/or propylene are prepolymerized in the presence of the catalyst composition prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578, European publication EP-A-279863, and PCT Publication WO 97/44371. A prepolymerized catalyst composition for purposes of this patent specification and appended claims preferably is a supported catalyst system.

The method for making the catalyst composition generally involves the combining, contacting, blending, and/or mixing of the respective catalyst components, optionally in the presence of the monomer or monomers to be polymerized. Ideally, the contacting is conducted under inert conditions at a temperature in the range of from 0 to 100° C., more preferably from 15 to 75° C., most preferably at about ambient temperature and pressure. The contacting is desirably performed under an inert gaseous atmosphere, such as nitrogen, however, it is also contemplated that the combination may be performed in the presence of olefin(s), solvents, hydrogen, and the like.

Mixing techniques and equipment contemplated for use in the method of the invention are well known. Mixing techniques may involve any mechanical mixing means, for example shaking, stirring, tumbling, and rolling. Another technique contemplated involves the use of fluidization, for example in a fluid bed reactor vessel where circulated gases provide the mixing.

For supported catalyst compositions, the catalyst composition is substantially dried and/or free flowing. In a preferred embodiment, the various components are contacted in a rotary mixer, tumble mixer, or in a fluidized bed mixing process, under a nitrogen atmosphere, and any liquid diluent is subsequently removed.

Suitable addition polymerization processes wherein the present catalyst compositions may be employed include solution, gas phase, slurry phase, high pressure, or combinations thereof. Particularly preferred is a solution or slurry polymerization of one or more olefins at least one of which is ethylene or propylene. The invention is particularly well suited to the polymerization of ethylene and/or propylene, optionally in combination with butene-1, pentene-1,4-methyl-pentene-1, hexene-1, octene-1, or decene-1.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbonadiene, isobutylene, vinylbenzocyclobutane, styrenes, alkyl substituted styrene, ethylidene norbornene, isoprene, dicyclopentadiene and cyclopentene.

Typically, in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. Examples of such processes are disclosed in U.S. Pat. Nos. 4,543,399, 4,588,790, 5,028,670, 5,317,036, 5,352,749, 5,405,922, 5,436,304, 5,453,471, 5,462,999, 5,616,661 and 5,668,228.

The reactor pressure in a gas phase process may vary from about 100 psig (700 kPa) to about 500 psig (3500 kPa), preferably in the range of from about 200 psig (1400 kPa) to about 400 psig (2800 kPa), more preferably in the range of from about 250 psig (1700 kPa) to about 350 psig (2400 kPa).

The reactor temperature in the gas phase process may vary from 30 to 120° C., preferably from 60 to 115° C., more preferably from 70 to 110° C., and most preferably from about 70 to 95° C.

A slurry polymerization process generally uses pressures in the range of from 100 kPa to 5 MPa, and temperatures in the range of 0 to 120° C. In a slurry polymerization, a suspension of solid, particulate polymer is formed in a liquid polymerization diluent to which monomers and often hydrogen along with catalyst are added. The diluent is intermittently or continuously removed from the reactor where the volatile components are separated from the polymer and recycled to the reactor. The liquid diluent employed should remain a liquid under the conditions of polymerization and be relatively inert. Preferred diluents are aliphatic or cycloaliphatic hydrocarbons, preferably propane, n-butane, isobutane, pentane, isopentane, hexane, cyclohexane, or a mixture thereof is employed. Examples of suitable slurry polymerization processes for use herein are disclosed in U.S. Pat. Nos. 3,248,179 and 4,613,484.

Examples of solution processes that are suitably employed with the catalyst compositions of the present invention are described in U.S. Pat. Nos. 4,271,060, 5,001,205, 5,236,998 and 5,589,555. Highly preferably the solution process is an ethylene polymerization or an ethylene/propylene copolymerization operated in a continuous or semi-continuous manner with high ethylene conversion, preferably greater than 98 percent ethylene conversion. Highly preferably such process is conducted at a temperature greater than or equal to 100° C., more preferably greater than or equal to 110° C., and most preferably greater than or equal to 115° C.

The polymers produced by the process of the invention can be used in a wide variety of products and end-use applications. The polymers produced by the process of the invention include high density polyethylenes, low density polyethylene, linear, low density polyethylene (ethylene/α-olefin copolymers), polypropylene, ethylene/propylene copolymers, and ethylene/propylene/diene terpolymers.

The ethylene homopolymers and copolymers formed by the present process preferably have a density in the range of from 0.85 g/cc to 0.97 g/cc, more preferably in the range of from 0.86 g/cc to 0.96 g/cc. Desirably they additionally have melt index ($I_2$) determined according to ASTM D-1238, Condition E, from 0.01 to 100 dg/min, preferably from 0.05 to 10 dg/min. Propylene homopolymers prepared according to the present process desirably have a Tm from 145–165° C., preferably from 150–160° C. Highly desirably polymers prepared according to the present invention are ethylene/propylene copolymers containing at least 60 percent, and preferably at least 80 percent polymerized propylene, and having a melt flow rate (MFR) determined according to ASTM D-1238, Condition L, from 0.1 to 500, preferably 0.1 to 100, more preferably 0.1 to 50, most preferred 1 to 30. Typically, the polymers produced by the process of the invention have a molecular weight distribution (Mw/Mn) from 1.5 to 15, preferably from 2 to 10.

The invention is further illustrated by the following Examples that should not be regarded as limiting of the present invention. Unless stated to the contrary or conventional in the art, all parts and percents are based on weight.

EXAMPLE 1

2-[N-(2,6-diisopropylphenylamido)-o-isopropylphenylmethyl]-6-(2-η-1-naphthyl)-pyridyl hafnium(IV) dimethyl

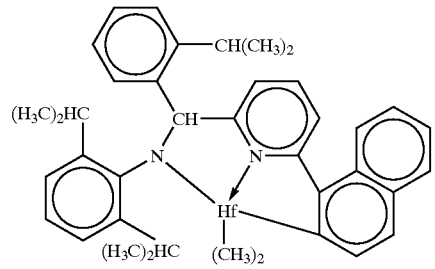

a) 2-Formyl-6-bromopyridine. This compound is synthesized according to literature procedures, *Tetrahedron Lett.*, (2001) 42, 4841.

b) 6-Bromo-2-(2,6-diisopropylphenyl)iminopyridine). A dry, 500 mL 3-neck round bottom flask is charged with a solution of 2-formyl-6-bromopyridine (72.1 g, 383 mmol) and 2,6-diisopropylaniline (72.5 g, 383 mmol) in 500 mL of anhydrous toluene containing 0.3 nm pore size molecular sieves (6 g) and 80 mg of p-TsOH. The reactor is equipped with a condenser, an over head mechanical stirrer and a thermocouple well. The mixture is heated to 70° C. under $N_2$ for 12 h. After filtration and removal of the volatiles under reduced pressure, a brown oil is isolated. Yield was 109 g, 81.9 percent.

GC/MS 346 ($M^+$), 331, 289, 189, 173, 159, 147, 131, 116, 103, 91, 78.

c) 6-(1-Naphthyl)-2-[(2,6-diisopropylphenyl)imino] pyridine. Naphthylboronic acid (54.5 g, 316 mmol) and $Na_2CO_3$ (83.9 g, 792 mmol) are dissolved into 200 mL of degassed 1:1 $H_2O$/EtOH. This solution is added to a toluene solution (500 mL) of 6-bromo-2-(2,6-diisopropylphenyl)-iminopyridine (109 g, 316 mmol). Inside of a dry box, 1 g (0.86 mmol) of tetrakis(triphenyl-phosphine)palladium(0) is dissolved in 50 mL of degassed toluene. The solution is removed from the dry box and charged into the $N_2$ purged reactor. The biphasic solution is vigorously stirred and heated to 70° C. for 4–12 hours. After cooling to room temperature, the organic phase is separated, the aqueous layer is washed with toluene (3×75 mL), the combined organic extracts are washed with $H_2O$ (3×200 mL) and dried over $MgSO_4$. After removing the volatiles under reduced pressure, the resultant light yellow oil is purified via recrystallization from methanol to give a yellow solid. Yield 109 g, 87.2 percent; mp 142–144° C.

$^1$H NMR (CDCl$_3$) δ 1.3 (d, 12H), 3.14 (m, 2H), 7.26 (m, 3H), 7.5–7.6 (m, 5H), 7.75–7.8 (m, 3H), 8.02 (m 1H), 8.48 (m, 2H). $^{13}$C NMR(CDCl$_3$) δ 23.96, 28.5, 119.93, 123.50, 124.93, 125.88, 125.94, 126.49, 127.04, 127.24, 128.18, 128.94, 129.7, 131.58, 134.5, 137.56, 137.63, 138.34, 148.93, 154.83, 159.66, 163.86. GC/MS 396 ($M^+$), 380, 351, 337, 220, 207, 189, 147.

d) 2-Isopropylphenyl lithium. Inside an inert atmosphere glovebox, n-butyl lithium (52.5 mmol, 21 mL of 2.5M in hexanes) is added by addition funnel over a period of 35–45 min to an ether solution (50 mL) of 2-isopropyl bromobezene (9.8 g, 49.2 mmol). After the addition is complete, the mixture is stirred at ambient temperature for 4 h. Then, the ether solvent is removed under vacuum overnight. The next day hexane is added to the remaining white solid and the mixture filtered, washed with additional hexane, and then vacuum dried. 2-Isopropylphenyl lithium (4.98 g, mmol) is collected as a bright white powder. A second crop of product (0.22 g) is later obtained from a second filtration of the original hexane filtrant.

$^1$H NMR (d$_8$-THF) δ 1.17 (d, J=6.8 Hz, 6H), 2.91 (sept, J=6.8, 1H), 6.62–6.69 (multiplets, 2H), 6.77 (d, J=7.3 Hz, 1H), 7.69 (multiplet, 1H). $^{13}$C NMR (d$_8$-THF) δ 25.99, 41.41, 120.19, 122.73, 122.94, 142.86, 160.73, 189.97.

e) 2-[N-(2,6-diisopropylphenylamino)-o-isopropylphenylmethyl]-6-(1-naphthyl)-pyridine. The imine, 6-(1-naphthyl)-2-[(2,6-diisopropylphenyl)imino]pyridine of step c) (2.20 g, 5.6 mmol) is magnetically stirred as a slurry in 60–70 mL of dry ether under a nitrogen atmosphere. An ether solution of 2-isopropylphenyl lithium (1.21 g, 9.67 mmol in about 25 mL dry ether) is added slowly using a syringe over a period of 4–5 min. After the addition is complete, a small sample is removed, quenched with 1N NH$_4$Cl and the organic layer analyzed by high pressure liquid chromatography (HPLC) to check for complete consumption of starting material. The remainder of the reaction is quenched by the careful, slow addition of 1N NH$_4$Cl (10 mL). The mixture is diluted with more ether and the organic layer washed twice with brine, dried (Na$_2$SO$_4$), filtered, and stripped of solvent under reduced pressure. The crude product obtained as a thick red oil (2.92 g; theoretical yield=2.87 g) is used without further purification.

$^1$H NMR (CDCl$_3$) δ 0.96 (d, J=6.6 Hz, 3H), 1.006 (d, J=6.8 Hz, 3H), 1.012 (d, J=6.8 Hz, 6H), 1.064 (d, J=6.8 Hz, 6H), 3.21–3.34 (multiplets, 3H), 4.87 (br s, NH), 5.72 (s, 1H), 6.98 (d, J=7.6 Hz, 1H) 7.00–7.20 (multiplets, 7H), 7.23–7.29 (multiplets, 4H), 7.51 (d, J=7.1 Hz 1H), 7.60–7.65 (multiplets, 2H), 7.75 (multiplet, 1H), 8.18 (multiplet, 1H). $^{13}$C NMR (CDCl$_3$) δ 23.80, 24.21, 24.24, 24.36, 28.10, 28.81, 67.08, 120.20, 122.92, 123.96, 124.42, 125.35, 125.81, 126.01, 126.28, 126.52, 126.58, 126.65, 127.80, 128.52, 128.62, 129.25, 131.82, 134.52, 136.81, 138.82, 140.94, 143.37, 143.41, 146.66, 159.05, 162.97.

f) 2-[N-(2,6-diisopropylphenylamido)-o-isopropylphenyl-methyl]-6-(2-η-1-naphthyl)-pyridylhafnium(IV) dichloride and 2-[N-(2,6-diisopropylphenylamido)-o-isopropylphenyl-methyl]-6-(2-η-1-naphthyl)-pyridylhafnium(IV) dimethyl A glass jar is charged with 8.89 mmol of the ligand from step e) dissolved in 30 mL toluene. To this solution is added 8.98 mmol of n-BuLi (2.5 M solution in hexanes) by syringe. This solution is stirred for 1 hour, then 8.89 mmol of solid HfCl$_4$ are added. The jar is capped with an air-cooled reflux condenser and the mixture is heated at reflux for about 1 hour. After cooling, 31.1 mmol of MeMgBr (3.5 equivalents, 3.0 M solution in diethyl ether) are added by syringe and the resulting mixture stirred overnight at ambient temperature. Solvent (toluene, hexanes and diethyl ether) is removed from the reaction mixture using a vacuum system attached to the drybox. Toluene (30 mL) is added to the residue and the mixture filtered, and the residue (magnesium salts) is washed with additional toluene (30 mL). Solvent is removed by vacuum from the combined toluene solution, and hexane is added, then removed by vacuum. Hexane is again added and the resulting slurry is filtered and the product washed with pentane to give the desired product as a yellow powder.

$^1$H NMR (C$_6$D$_6$): δ 8.58 (d, J=7.8 Hz, 1H), 8.25 (d, J=8.4 Hz, 1H), 7.82 (d, J=7.5 Hz, 1H), 7.72 (d, J=6.9 Hz, 1H), 7.50 (d, J=8.1 Hz, 1H), 7.36–7.27 (multiplets, 3H), 7.19–6.99 (multiplets, 7H), 6.82 (t, J=8.1 Hz, 1H), 6.57 (s, 1H), 6.55 (d, J=7.8 Hz, 1H), 3.83 (septet, J=6.9 Hz, 1H), 3.37 (septet, J=6.9 Hz, 1H), 2.89 (septet, J=6.9 Hz, 1H), 1.38 (d, J=6.6 Hz, 3H), 1.37 (d, J=6.9 Hz, 3H), 1.17 (d, J=6.9 Hz, 3H), 1.15 (d, J=7.2 Hz, 3H), 0.96 (s, 3H), 0.70 (s, 3H), 0.69 (d, J=5.4 Hz, 3H), 0.39 (d, J=6.9 Hz, 3H).

EXAMPLE 2

2-[N-(2,6-diisopropylphenylamido)-o-cyclohexylphenylmethyl]-6-(2-η-1-naphthyl)pyridyl hafnium(IV) dimethyl

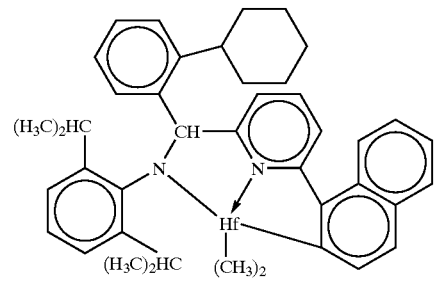

The reaction conditions of Example 1 are substantially repeated excepting that 2-[N-(2,6-diisopropylphenylamino)-o-cyclohexylphenylmethyl]-6-(1-naphthyl)pyridine (prepared by reaction of the imine, 6-(1-naphthyl)-2-[(2,6-diisopropylphenyl)imino]pyridine with 2-cyclohexylphenyl lithium in diethylether) is reacted with HfCl$_4$.

EXAMPLE 3

2-[N-(4-chloro-2,6-diisopropylphenylamido)-o-cyclohexylphenylmethyl]-6-(2-η-1-(4-chlorophenyl))pyridyl hafnium(IV) dimethyl

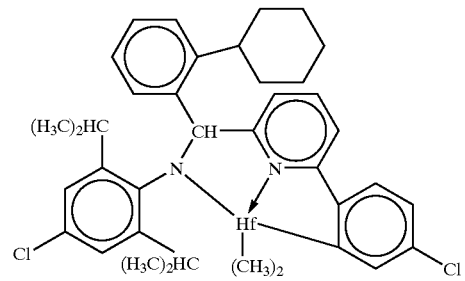

The reaction conditions of Example 1 are substantially repeated excepting that 2-[N-(4-chloro-2,6-diisopropylphenylamino)-o-cyclohexylphenylmethyl]-6-(4-chlorophenyl)-pyridine (prepared by reaction of the imine, 6-(4-chlorophenyl)-2-[(4-chloro-2,6-diisopropylphenyl)imino]pyridine with 2-cyclohexylphenyl lithium in diethylether) is reacted with HfCl$_4$.

EXAMPLE 4

2-[N-(4-chloro-2,6-diisopropylphenylamido)-o-isopropylphenylmethyl]-6-(2-η-1-naphthyl)pyridyl hafnium(IV) dimethyl

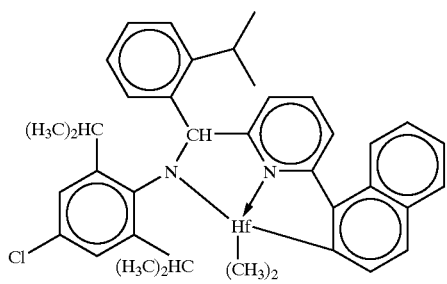

The reaction conditions of Example 1 are substantially repeated excepting that 2-[N-(4-chloro-2,6-diisopropylphenylamino)-o-isopropylphenylmethyl]-6-(1-naphthyl)pyridine (prepared by reaction of the imine, 6-(1-naphthyl)-2-[(4-chloro-2,6-diisopropylphenyl)imino]-pyridine with 2-isopropylphenyl lithium in diethylether) is reacted with HfCl$_4$.

EXAMPLE 5

2-[N-(4-chloro-2,6-diisopropylphenylamido)-o-cyclohexyphenylmethyl]-6-(2-η-1-naphthyl)pyridyl hafnium(IV) dimethyl

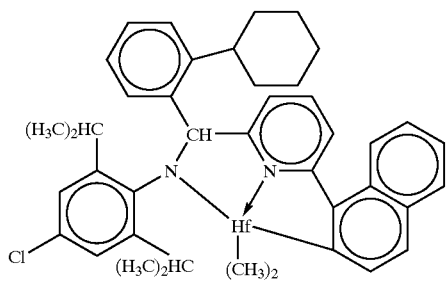

The reaction conditions of Example 1 are substantially repeated excepting that 2-[N-(4-chloro-2,6-diisopropylphenylamino)-o-cyclohexylphenylmethyl]-6-(1-naphthyl)pyridine (prepared by reaction of the imine, 6-(1-naphthyl)-2-[(4-chloro-2,6-diisopropylphenyl)imino]-pyridine with 2-cyclohexylphenyl lithium in diethylether) is reacted with HfCl$_4$.

EXAMPLE 6

2-[N-(2,6-diisopropylphenylamido)-o-isopropylphenylmethyl]-6-(2-η-1-naphthyl)pyridyl zirconium(IV) dimethyl

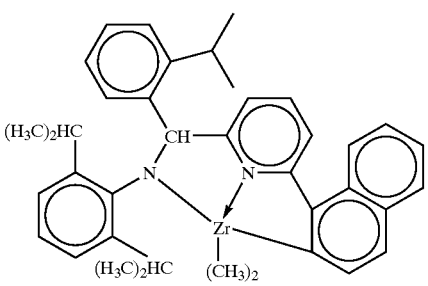

The reaction conditions of Example 1 are substantially repeated excepting that 2-[N-(2,6-diisopropylphenylamino)-o-isopropylphenylmethyl]-6-(1-naphthyl)pyridine (prepared by reaction of the imine, 6-(1-naphthyl)-2-[(2,6-diisopropylphenyl)imino]pyridine with 2-isopropylphenyl lithium in diethylether) is reacted with ZrCl$_4$.

EXAMPLE 7

2-[N-(2,6-diisopropylphenylamido)-o-(t-butylphenyl)methyl]-6-(2-η-1-(naphthyl)pyridyl hafnium(IV) dimethyl

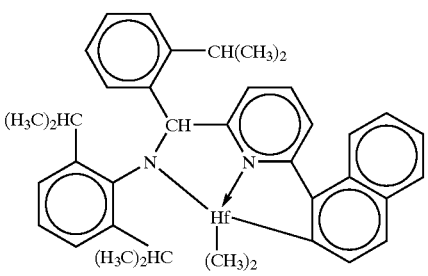

The reaction conditions of Example 1 are substantially repeated excepting that 2-[N-(2,6-diisopropylphenylamino)-o-(t-butylphenyl)methyl]-6-(1-naphthyl)pyridine (prepared by reaction of the imine, 6-(1-naphthyl)-2-[(2,6-diisopropylphenyl)imino]pyridine with 2-(t-butyl)phenyl lithium in diethylether) is reacted with HfCl$_4$.

EXAMPLE 8

2-[N-(2,6-diisopropylphenylamido)-o-(isopropylphenyl)methyl]-6-(2-η-1-(naphthyl)pyridyl hafnium(IV) bis(tri(methyl)silylmethyl)

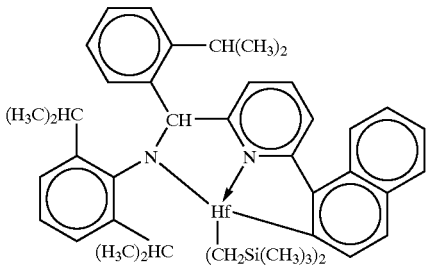

The reaction conditions of Example 1 are substantially repeated excepting that 2-[N-(2,6-diisopropylphenylamino)-o-isopropylphenylmethyl]-6-(2-η-1-naphthyl)pyridyl hafnium(IV) dichloride is reacted at room temperature with excess Li(CH$_2$(Si(CH$_3$)$_3$) in toluene overnight. The resulting slurry is filtered, stripped of toluene, reslurried in hexane, and filtered. The resulting solid product is dissolved in benzene, filtered again, and the benzene removed to give the desired product.

EXAMPLE 9

2-[N-(2,6-diisopropylphenylamido)-o-(isopropylphenyl)methyl]-6-(2-η-1-(naphthyl)pyridyl hafnium(IV) dichloride In a glovebox, 150 mg (0.217 mmol) of 2-[N-(2,6-diisopropylphenylamido)-o-(isopropylphenyl)methyl]-6-(2-η-1-(naphthyl)pyridyl hafnium(IV) dimethyl (Example 1) and 60.0 mg (0.436 mmol) of [HNEt$_3$]Cl are stirred in 15 mL of toluene for 6 days at 25° C. The solution is passed through a poly(tetrafluoroethylene) syringe filter and the volatiles are removed under reduced pressure. The crude product is washed twice with hexane and recovered by drying under reduced pressure. Isolated yield is 105 mg (66 percent).

Comparative A 2-[N-(2,6-diisopropylphenylamido)-o-methylphenylmethyl]-6-(2-η-1-(naphthyl)pyridyl hafnium(IV) dimethyl

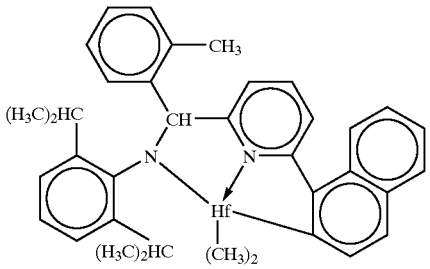

The reaction conditions of Example 1 are substantially repeated excepting that 2-[N-(2,6-diisopropylphenylamino)-o-methylphenylmethyl]-6-(1-naphthyl)pyridine (prepared by reaction of the imine, 6-(1-naphthyl)-2-[(2,6-diisopropylphenyl)imino]pyridine with 2-methylphenyl lithium in diethylether) is reacted with HfCl$_4$.

Comparative B 2-[N-(2,6-diisopropylphenylamido)-o-phenylphenylmethyl]-6-(2-η-1-(naphthyl)pyridyl hafnium(IV) dimethyl

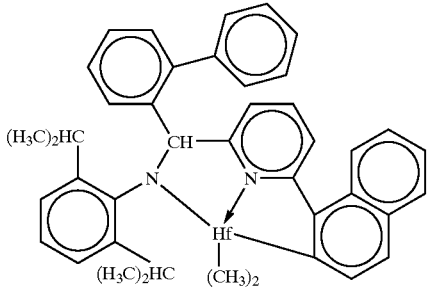

A 100 mL 3-neck flask, equipped with magnetic stirrer and a N$_2$ sparge, is charged with 6-(1-naphthyl)pyridine-2-(2,6-diisopropylphenyl)imine (6.8 g, 17.1 mmol) and 100 mL of anhydrous, degassed toluene. The solution is cooled to −40° C. after which a solution of o-biphenyllithium (3.43 g, 21.5 mmol) is added dropwise over 5 minutes. After warming to room temperature over 1 hour the solution is stirred at room temperature for 1 hour. The reaction is then quenched with 20 mL of aq. NH$_4$Cl. The organic layer is separated and washed three times with 100 mL quantities of water. Evaporation of the solvent gives the product as an off white solid. The solid amine is redissolved into methylenechloride, eluted through a bed of neutral alumina with hexanes, and recovered by drying to yield 5.3 g of a white solid (56.4 percent).

To form the metal complex, the reaction conditions of Example 1 are substantially repeated excepting that 2-[N-(2,6-diisopropylphenylamino)-o-phenylphenylmethyl]-6-(1-naphthyl)pyridine is reacted with HfCl$_4$.

Polymerization Runs 1–21

Polymerizations are conducted in a computer controlled, stirred, jacketed 1.8 L stainless steel autoclave solution batch reactor. The bottom of the reactor is fitted with a large orifice bottom dump valve, which empties the reactor contents into a 6 L stainless steel container. The container is vented to a 30 gal. blowdown tank, with both the container and the tank are purged with nitrogen. All chemicals used for polymerization or catalyst makeup are run through purification columns, to remove any impurities. Propylene and mixed alkanes solvent (Isopar E™ available from Exxon Mobil Chemicals Inc.), or toluene, are passed through 2 columns, the first containing alumina, the second containing a purifying reactant (Q5™ available from Englehardt Corporation). Nitrogen and hydrogen gases are passed through a single column containing Q5™ reactant.

The autoclave is cooled to 25° C. before loading. It was charged with about 667 g mixed alkanes, hydrogen (using a calibrated 50 mL shot tank and a differential pressure in the shot tank of 0.41 MPa), followed by 286 g of propylene using a micro-motion flowmeter. The reactor is then brought to 90° C. or 120° C. before addition of catalyst composition.

The metal complex (catalyst) (1.0 μmole) is dissolved in 5 ml toluene. The metal complex and hexane solutions of activator and tertiary component are handled in an inert glovebox, mixed together in a vial, drawn into a syringe and pressure transferred into the catalyst shot tank. This is followed by 3 rinses of toluene, 5 mL each. The cocatalyst used is a long-chain alkyl ammonium borate of approximate stoichiometry equal to methyldi(octadecyl)ammonium tetrakis(pentafluorophenyl)borate (MDB). The tertiary component used is tri(i-propyl)aluminum modified methylalumoxane (PMAO-IP™, available from Akzo Noble, Inc.) (MAO) or di(n-octyl)aluminum 2,6-di-t-butyl-4-methylphenoxide (DAP) in a molar ratio (metal complex:cocatalyst: tertiary component) of 1:1.2:30. The shot tank is pressurized with $N_2$ to >0.6 MPa above the reactor pressure, and the contents are quickly blown into the reactor. Both reaction exotherm and pressure drop are monitored throughout the reaction run time.

After 10 minutes polymerization, the agitator is stopped, the reactor pressure is increased to about 3.4 MPa with $N_2$, and the bottom dump valve opened to empty reactor contents to the collection vessel. The contents are poured into trays and placed in a lab hood where the solvent is evaporated overnight. The trays are then transferred to a vacuum oven, where they are heated to 145° C. under vacuum to remove any remaining solvent. After the trays cooled to ambient temperature, the polymers are quantified and analyzed.

Runs in groups 1–4, 5–6, 7–8, 9–10, 11–14, 15–18, 19, and 20–21 were conducted at different times and are not intended for use in comparisons between groups. Results are contained in Table 1.

TABLE 1

| Run | Catalyst | Tert. Comp. | Temp. (° C.) | Yield (g) | Efficiency (g poly./g Hf) | Tm (° C.) | Mw | Mw/Mn |
|---|---|---|---|---|---|---|---|---|
| 1 | Ex. 1[1] | MAO | 90 | 42.4 | 294,000 | 153.2 | 229,000 | 2.22 |
| 2 | Ex. 2[2] | " | " | 52.3 | 293,000 | 151.8 | 234,000 | 2.20 |
| 3 | Ex. 3[3] | " | " | 34 | 190,000 | 150.0 | 558,000 | 2.78 |
| 4* | comp. A[4] | " | " | 40.6 | 227,000 | 148.2 | 179,000 | 2.03 |
| 5 | Ex. 4[5] | " | " | 34.7 | 194,000 | 153.2 | 281,000 | 2.14 |
| 6 | Ex. 5[6] | " | " | 35.8 | 201,000 | 151.8 | 296,000 | 2.21 |
| 7 | Ex. 6[7] | " | " | 7.0 | 77,000[12] | 147.5 | 52,000 | 2.12 |
| 8* | comp. A[4] | " | " | 35.7 | 200,000 | — | — | — |
| 9 | Ex. 7[8] | " | " | 15.1 | 85,000 | 155.4 | 77,000 | — |
| 10* | comp. A[4] | " | " | 48.3 | 271,000 | — | — | — |
| 11 | Ex. 1[1] | MAO | " | 45.6 | 255,000 | — | — | — |
| 12 | " | DAP | " | 54.4 | 305,000 | — | — | — |
| 13* | comp. A[4] | MAO | " | 26.9 | 151,000 | — | — | — |
| 14* | " | DAP | " | 36.4 | 204,000 | — | — | — |
| 15 | Ex. 1[1] | MAO | 120 | 9.7 | 54,000 | 146.8 | 104,000 | 3.93 |
| 16 | Ex. 2[2] | " | " | 9.2 | 52,000 | 147.0 | 108,000 | 4.65 |
| 17 | Ex. 3[3] | " | " | 6.1 | 34,000 | 145.8 | 265,000 | 6.52 |
| 18* | comp. A[4] | " | " | 6.1 | 34,000 | 143.6 | 84,000 | 4.99 |
| 19* | comp. B[9] | " | 90 | 145[11] | 203,000 | 149.2 | 385,000 | 2.12 |
| 20 | Ex. 8[10] | " | " | 67.7 | 379,000 | 150.3 | — | — |
| 21* | Comp. A[4] | " | " | 33.9 | 190,000 | — | — | — |

*comparative, not an example of the invention
[1]2-[N-(2,6-diisopropylphenylamido)-o-isopropylphenylmethyl]-6-(2-η-1-naphthyl)-pyridyl hafnium(IV) dimethyl
[2]2-[N-(2,6-diisopropylphenylamido)-o-cyclohexylphenylmethyl]-6-(2-η-1-naphthyl)pyridyl hafnium(IV) dimethyl
[3]2-[N-(4-chloro-2,6-diisopropylphenylamido)-o-cyclohexylphenylmethyl]-6-(2-η-1-(4-chlorophenyl))pyridyl hafnium(IV) dimethyl
[4]2-[N-(2,6-diisopropylphenylamido)-o-methylphenylmethyl]-6-(2-η-1-(naphthyl)pyridyl hafnium(IV) dimethyl
[5]2-[N-(4-chloro-2,6-diisopropylphenylamido)-o-isopropylphenylmethyl]-6-(2-η-1-naphthyl) pyridyl hafnium(IV) dimethyl
[6]2-[N-(4-chloro-2,6-diisopropylphenylamido)-o-cyclohexylphenylmethyl]-6-(2-η-1-naphthyl) pyridyl hafnium(IV) dimethyl
[7]2-[N-(2,6-diisopropylphenylamido)-o-isopropylphenylmethyl]-6-(2-η-1-naphthyl)pyridyl zirconium(IV) dimethyl
[8]2-[N-(2,6-diisopropylphenylamido)-o-(t-butylphenyl)methyl]-6-(2-η-1-(naphthyl)pyridyl hafnium(IV) dimethyl
[9]2-[N-(2,6-diisopropylphenylamido)-o-phenylphenylmethyl]-6-(2-η-1-(naphthyl)pyridyl hafnium(IV) dimethyl
[10]2-[N-(2,6-diisopropylphenylamido)-o-isopropylphenylmethyl]-6-(2-η-1-(naphthyl)pyridyl hafnium(IV) bis(tri(methyl)silylmethyl)
[11]polymerization conducted in different reactor, 4.0 μmole Hf
[12]For run 7, Efficiency = (g polymer/g Zr).

Polymerization Runs 22–30

The 90° C. polymerization conditions of Runs 1–21 are substantially repeated using different cocatalyst/tertiary component combinations. The cocatalysts tested are MDB, the methyldi($C_{14-20}$ alkyl)ammonium salt of bis(tris (pentafluorophenyl)alumane)-2-undecylimidazolide (MBU) or the methyldi($C_{14-20}$ alkyl)ammonium salt of bis(tris (pentafluorophenyl)alumane)imidazolide (MBI), both salts having been prepared according to the teachings of U.S. Pat.

No. 6,395,671. The tertiary compounds tested were MAO, DAP and triethylaluminum (TEA). The results are contained in Table 2.

removed from the exit stream, and the product is recovered by extrusion using a devolatilizing extruder. The extruded strand is cooled under water and chopped into pellets.

TABLE 2

| Run | Catalyst | Cocat. | Tert. Comp. | Yield (g) | Efficiency (g poly./g Hf) | Mw | Mw/Mn |
|---|---|---|---|---|---|---|---|
| 22 | Ex. 1[1] | MDB | MAO | 50.5 | 283,000 | 238,000 | 1.84 |
| 23 | " | MBU | " | 66.7 | 374,000 | 207,000 | 2.10 |
| 24 | " | " | DAP | 70.1 | 393,000 | 196,000 | 2.05 |
| 25 | " | " | TEA | 72.5 | 406,000 | 181,000 | 2.12 |
| 26 | " | MBI | MAO | 65.6 | 368,000 | 173,000 | 2.02 |
| 27* | comp. A[2] | MDB | " | 38.9 | 218,000 | 182,000 | 2.33 |
| 28* | " | MBU | " | 54.6 | 306,000 | 166,000 | 2.41 |
| 29* | " | " | DAP | 63.2 | 354,000 | 176,000 | 1.89 |
| 30* | " | " | TEA | 74.0 | 415,000 | 172,000 | 1.94 |

*comparative, not an example of the invention
[1]2-[N-(2,6-diisopropylphenylamido)-o-isopropylphenylmethyl]-6-(2-η-1-naphthyl)-pyridyl hafnium(IV) dimethyl
[2]2-[N-(2,6-diisopropylphenylamido)-o-methylphenylmethyl]-6-(2-η-1-naphthyl)pyridyl hafnium(IV) dimethyl Continuous Solution Polymerizations, Runs 31–38

Continuous polymerizations are carried out in a computer controlled autoclave reactor equipped with an internal stirrer. Purified toluene solvent, ethylene (where used), hydrogen, and propylene are supplied to a 3.8 L reactor equipped with a jacket for temperature control and an internal thermocouple. The solvent feed to the reactor is measured by a mass-flow controller. A variable speed diaphragm pump controls the solvent flow rate and pressure to the reactor. The propylene feed is measured by a mass flow meter and the flow is controlled by a variable speed diaphragm pump. At the discharge of the pump, a side stream is taken to provide flush flows for the catalyst injection line and the reactor agitator. The remaining solvent is combined with hydrogen and delivered to the reactor. A mass flow controller is used to deliver hydrogen into the reactor as needed. The temperature of the solvent/monomer is controlled by use of a heat exchanger before entering the reactor. This stream enters the bottom of the reactor. The catalyst component solutions are metered using pumps and mass flow meters, and are combined with the catalyst flush solvent. This stream enters the bottom of the reactor, but in a different port than the port used for the monomer stream. The reactor is run liquid-full at 500 psig (3.45 MPa) with vigorous stirring. The process flow enters the bottom and exits the top of the reactor. All exit lines from the reactor are steam traced and insulated. Polymerization is stopped with the addition of a small amount of water, and other additives and stabilizers can be added without stopping stirring within the reactor. The stream flows through a static mixer and a heat exchanger in order to heat the solvent/polymer mixture. The solvent and unreacted monomers are continuously The following experimental conditions are employed in producing polypropylene homopolymer. Reactor temperature is set at 100° C., solvent is adjusted to provide 16–18 percent solids, and propylene is regulated to provide 50 percent propylene conversion. The quantity of hydrogen is adjusted to make a product having a melt flow rate (MFR) determined according to ASTM D-1238, condition L (2.16 kg, 230 degrees C.) of about 10 using comparative A catalyst. After reaching stable operating conditions, product is collected for 3 hours. For subsequent polymerizations the same hydrogen level is maintained, thereby altering the MFR of the resulting product, excepting that for run 33, additional hydrogen is added to the reactor to increase the MFR to a level capable of processing by available equipment. Results are contained in Table 3.

TABLE 3

| Run | Catalyst | Efficiency (g poly./g Hf) | MFR | $H_2$ SCCM[1] | Density (g/cm$^3$) | Tm (° C.) | Mw | Mw/Mn |
|---|---|---|---|---|---|---|---|---|
| 31 | Ex. 1 | 788,000 | 5.36 | 6.00 | 0.904 | 149.7 | 247,000 | 2.3 |
| 32 | Ex. 2 | 723,000 | 6.09 | 6.00 | 0.902 | 148.6 | 243,000 | 2.2 |
| 33 | Ex. 3 | 494,000 | 2.71 | 12.90 | 0.904 | 147.9 | 307,000 | 3.7 |
| 34* | Comp. A | 556,000 | 10.85 | 6.00 | 0.904 | — | — | — |

*comparative, not an example of the invention
[1]standard cm$^3$/minute

For propylene/ethylene copolymers, reactor conditions are again optimized for use of Comparative A catalyst. Reactor temperature is set at 110° C., solvent flow is adjusted to provide 16–18 percent solids, and propylene is regulated to provide 50 percent propylene conversion. The quantity of hydrogen is adjusted to make a product having MFR of approximately 10. The purified ethylene is measured with a mass flow meter, controlled with a control valve, and incorporated into the solvent/hydrogen stream. Ethylene content of the resulting copolymer is 6.2 percent in all runs. For subsequent polymerizations the same hydrogen level is maintained, thereby altering the MFR of the resulting product, excepting that for run 37, additional hydrogen is added to the reactor to increase the MFR to a level capable of processing by available equipment. Results are contained in Table 4.

TABLE 4

| Run | Catalyst | Efficiency (g poly./g Hf) | MFR | H$_2$ SCCM[1] | Density (g/cm$^3$) | Tm (° C.) | Mw | Mw/Mn |
|---|---|---|---|---|---|---|---|---|
| 35 | Ex. 1 | 593,000 | 5.68 | 9.00 | 0.880 | 83.2 | 228,000 | 2.5 |
| 36 | Ex. 2 | 660,000 | 4.60 | 9.00 | 0.879 | 81.6 | 231,000 | 2.3 |
| 37 | Ex. 3 | 263,000 | 2.52 | 20.00 | 0.878 | 81.3 | 292,000 | 4.4 |
| 38* | Comp. A | 442,000 | 10.73 | 9.00 | 0.879 | 100.6 | — | — |

*comparative, not an example of the invention
[1]standard cm$^3$/minute

What is claimed is:

1. A metal complex corresponding to the formula:

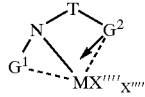

(IA)

wherein

G$^1$ is selected from alkyl, cycloalkyl, aryl, aralkyl, alkaryl, heteroalkyl, heterocycloalkyl, heteroaryl, heteroaralkyl, heteroalkaryl, silyl, and inertly substituted derivatives thereof containing from 1 to 40 atoms not counting hydrogen;

T is a divalent bridging group of from 10 to 30 atoms not counting hydrogen, selected from mono- or di- aryl-substituted methylene or silylene groups or mono- or di-heteroaryl-substituted methylene or silylene groups, wherein at least one such aryl- or heteroaryl-substituent is substituted in one or both ortho-positions with a secondary or tertiary alkyl-group, a secondary or tertiary heteroalkyl group, a cycloalkyl group, or a heterocycloalkyl group, G$^2$ is a C$_{6-20}$ heteroaryl group containing Lewis base functionality;

M is the Group 4 metal;

X"" is an anionic, neutral or dianionic ligand group;

x"" is a number from 0 to 5 indicating the number of X"" groups, and bonds, optional bonds and electron donative interactions are represented by lines, dotted lines and arrows respectively.

2. A metal complex according to claim 1 corresponding to the formula:

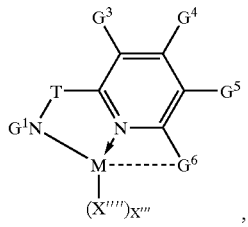

(IIA)

wherein

M, X"", x"", G$^1$ and T are as previously defined,

G$^3$, G$^4$, G$^5$ and G$^6$ are hydrogen, halo, or an alkyl, aryl, aralkyl, cycloalkyl, or silyl group, or a substituted alkyl-, aryl-, aralkyl-, cycloalkyl-, or silyl-group of up to 20 atoms not counting hydrogen, or adjacent G$^3$, G$^4$, G$^5$ or G$^6$ groups may be joined together thereby forming fused-ring derivatives, and bonds, optional bonds and electron pair donative interactions are represented by lines, dotted lines and arrows respectively.

3. A metal complex according to claim 2 corresponding to the formula:

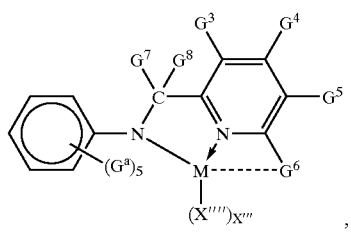

(IIIA)

wherein

M, X"", x"", G$^3$, G$^4$, and G$^5$ are as previously defined,

G$^6$ is C$_{6-20}$ aryl, aralkyl, alkaryl, or a divalent derivative thereof;

G$^a$ independently each occurrence is hydrogen, C$_{1-20}$ alkyl, or halo;

G$^7$ and G$^8$ independently each occurrence are hydrogen or a C$_{1-30}$ alkyl, aryl, aralkyl, heteroalkyl, heteroaryl, or heteroaralkyl group, with the proviso that at least one of G$^7$ or G$^8$ is a C$_{10-30}$ aryl or heteroaxyl group substituted in one or both ortho-positions with a secondary or tertiary alkyl- or cycloalkyl-ligand; and bonds, optional bonds and electron pair donative interactions are represented by lines, dotted lines and arrows respectively.

4. A metal complex according to claim 3 corresponding to the formula:

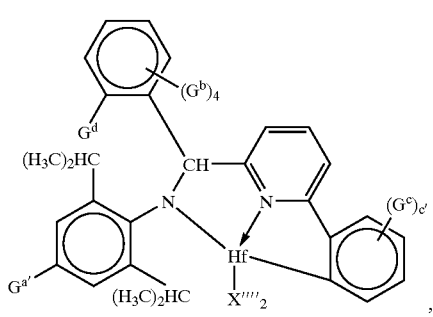

(IVA)

wherein

X"" each occurrence is halide, N,N-di(C$_{1-4}$alkyl)amido, C$_{1-20}$ aralkyl, C$_{1-20}$ alkyl, C$_{5-20}$ cycloalkyl, or tri(C$_{1-4}$)alkylsilyl; a tri(C$_{1-4}$)alkylsilyl-substituted C$_{1-10}$ hydrocarbyl group; or two X"" groups together are a C$_{4-40}$ conjugated diene;

$G^{a'}$ is hydrogen, $C_{1-20}$ alkyl or chloro;

$G^b$ independently each occurrence is hydrogen, $C_{1-20}$ alkyl, aryl, or aralkyl or two adjacent $G^b$ groups are joined together thereby forming a ring;

$G^c$ independently each occurrence is hydrogen, halo, $C_{1-20}$ alkyl, aryl, or aralkyl, or two adjacent $G^c$ groups are joined together thereby forming a ring, c is 1–5 and c' is 1–4;

$G^d$ is isopropyl or cyclohexyl; and bonds and electron pair donative interactions are represented by lines and arrows respectively.

5. A metal complex according to claim 4 corresponding to the formula:

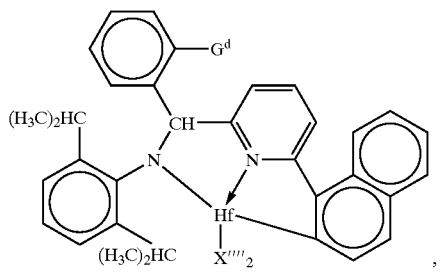

(VA)

wherein

X"" each occurrence is methyl, chloro, or tri(methyl)silylmethyl, and $G^d$ is isopropyl or cyclohexyl.

6. An addition polymerization catalyst composition comprising a metal complex according to any one of claims 1–5 and an activating cocatalyst.

7. A composition according to claim 6 wherein the activating cocatalyst consists of a compound or mixture selected from the group consisting of alkylalumoxanes, tetrakis(pentafluorophenyl)borate, and mixtures thereof.

8. An addition polymerization process wherein one or more olefin monomers are contacted with a catalyst composition under polymerization conditions, characterized in that the catalyst composition is a composition according to claim 6.

9. A process according to claim 8 which is a solution polymerization process.

10. A process according to claim 8 wherein propylene is homopolymerized or propylene and ethylene are copolymerized.

* * * * *